(12) United States Patent
Altshuler et al.

(10) Patent No.: US 6,648,904 B2
(45) Date of Patent: Nov. 18, 2003

(54) METHOD AND APPARATUS FOR CONTROLLING THE TEMPERATURE OF A SURFACE

(75) Inventors: Gregory Altshuler, Wilmington, MA (US); James Burke, III, Londonderry, NH (US)

(73) Assignee: Palomar Medical Technologies, Inc., Burlington, MA (US)

( * ) Notice: Subject to any disclaimer, the term of this patent is extended or adjusted under 35 U.S.C. 154(b) by 0 days.

(21) Appl. No.: 09/996,662

(22) Filed: Nov. 29, 2001

(65) Prior Publication Data

US 2003/0100936 A1 May 29, 2003

(51) Int. Cl.$^7$ .................................................. A61F 7/00
(52) U.S. Cl. .............................. 607/96; 492/46; 601/15
(58) Field of Search .............................. 601/20, 19, 15; 607/96, 147; 492/46

(56) References Cited

U.S. PATENT DOCUMENTS

| | | | | | |
|---|---|---|---|---|---|
| 622,350 A | * | 4/1899 | Hans | ............................ | 601/19 |
| 926,245 A | * | 6/1909 | Coon | ............................ | 601/19 |
| 1,270,635 A | * | 6/1918 | Ljungstrom | ................... | 601/19 |
| 1,882,370 A | * | 10/1932 | Schroeder | ..................... | 601/19 |
| 2,472,385 A | * | 6/1949 | Rollman | ....................... | 601/19 |
| 4,745,909 A | * | 5/1988 | Pelton et al. | .................. | 601/15 |
| 4,884,560 A | * | 12/1989 | Kuracina | ...................... | 601/15 |
| 5,127,395 A | * | 7/1992 | Bontemps | .................... | 601/19 |
| 5,267,399 A | * | 12/1993 | Johnston | ...................... | 601/19 |
| 6,236,891 B1 | * | 5/2001 | Ingle et al. | .................... | 30/41 |

* cited by examiner

Primary Examiner—Lee Cohen
Assistant Examiner—Henry M. Johnson
(74) Attorney, Agent, or Firm—Thomas J. Engellenner; Deborah A. Miller; Nutter McClennen & Fish LLP (57) ABSTRACT

A method and apparatus are provided for controlling the temperature of a surface to preheat or precool the surface, to heat or cool the surface to effect a therapeutic treatment or to post-heat or post-cool the surface. A roller, preferably mounted to a handle, is provided which contains a material which is heated or cooled prior to treatment as appropriate so as to undergo a phase change and is then rolled over the surface the temperature of which is to be controlled, gradually undergoing a phase change to return to its initial state as it is rolled over the surface to effect the desired heating or cooling of the surface. The roller preferably has a large internal surface area in contact with the material undergoing the phase change.

32 Claims, 5 Drawing Sheets

METHOD AND APPARATUS FOR CONTROLLING THE TEMPERATURE OF A SURFACE

FIELD OF THE INVENTION

This invention relates to methods and apparatus for selectively controlling the temperature of a surface, and more particularly to a roller adapted to cool or heat a surface as it is rolled thereover and to methods for the utilization of such roller.

BACKGROUND OF THE INVENTION

There are numerous applications, both in medically related fields, and in industry where a need exists to cool or heat a surface, for example a patient's skin, to a selected temperature either to achieve a desired therapeutic or other result, to precool the surface prior to the performance of some other procedure which normally causes heating of the surface, the precooling reducing pain and raising the damage threshold of the surface during such procedure, or to preheat the surface prior to the performance of another procedure to facilitate the performance of such procedure. For example, in the medical area, cooling of the surface of the patient's skin may be desirable in the early treatment of mild burns, to at least partially numb the skin to reduce pain or itching or for some other purpose. Rapid cooling of a surface may also be desirable in certain industrial applications.

However, the cooling of a surface is most useful in medical or industrial applications where a treatment to be applied either to or preferably through such surface results in the heating thereof. Precooling the skin surface in such applications can reduce pain and raise the damage threshold for the skin. For example, where a laser or other optical radiation source is applied to a patient's skin to perform dermatology procedures such as hair removal, treatment of vascular or pigmented lesions, skin rejuvenation and the like, it is desirable that at least the epidermis of the patient's skin be precooled to a temperature below normal body temperature, approximately 37° C., to reduce patient pain and discomfort and to protect the epidermis from thermal damage. Depending on the procedure performed, such precooling may be adequate to protect the patient's skin without requiring additional cooling during the performance of the procedure. In any event, such precooling will enhance the effectiveness of cooling provided during the performance of the procedure and/or reduce the thermal load imposed on any cooling mechanism operable during the performance of the procedure. There are also applications where post-cooling of a surface (ie, cooling of a surface after treatment) may be desirable to, for example, reduce pain, reduce thermal damage and/or reduce swelling.

Numerous procedures have been employed in the past for cooling or precooling the surface of a patient's skin or other surface, for example putting an ice cube, ice pack or the like in contact with such surface, spraying such surface with a cryogen fluid or placing a device cooled thermoelectrically or by a flowing fluid in contact with the surface to be cooled. However, ice cubes are messy and may result in a water barrier between the solid ice and the skin which impedes cooling. Ice bags generally do not cool uniformly, have limited cooling capacity and thaw relatively quickly. Further, as the ice thaws, ice is less likely to be in contact with the portion of the ice bag in contact with the person's skin, thereby significantly reducing the effectiveness of the ice bag as a cooling medium. Cryogen in contact with the patient's skin may result in the skin being cooled below the desired temperature and this form of cooling is not easy to control. The other forms of contact cooling are generally more complex and expensive, both to purchase and to use, and are therefore not ideal for many applications; in particular, they generally are not suitable for quickly covering a large surface area.

Similarly, heating of a surface is frequently utilized to perform a selected therapeutic function, such as for relief of muscle aches or to relax collagen coils to permit reconfiguration of skin features such as wrinkles. Preheating of skin or another surface may be utilized to facilitate a heat treatment procedure to be subsequently performed by a radiation or other heating source, for example permitting a lower power source to be used for such function or permitting greater control in the performance of such function.

Heating or cooling may also be used in conjunction with massage to treat muscle, joint and other problems.

A need therefore exists for an improved mechanism for quickly cooling, precooling, heating, preheating, post-cooling or post-heating a surface, in particular the surface of a patient's skin, over a relatively large area to a substantially uniform and relatively controlled temperature, which mechanism is both easy to use and relatively inexpensive. In some applications, particularly where the surface is a patient's skin, it may also be desirable to apply pressure to the skin in conjunction with the temperature control function so as to temporarily remove blood from the treatment area, thereby reducing the moderating effect of profusion on the desired temperature change. Pressure may also perform a massage function which may be desirable in certain applications, particularly for the treatment of sore muscles or other aches and pains. Further, there is frequently a need to spread a thin layer of an impedance matching liquid or of some other substance over the patient's skin or other surface prior to treatment. It would be desirable if the same mechanism used to cool or heat the patient's skin could also be utilized to facilitate the uniform spreading of a thin layer of such substance over the surface.

SUMMARY OF THE INVENTION

In accordance with the above, this invention provides, in accordance with one aspect thereof, a device for cooling or otherwise controlling the temperature of a surface, which device includes a roller formed of a material having good heat transfer properties, for example a metal such as copper or aluminum, the roller having an external surface, which may be cylindrical, may have a plurality of faces, for example flat faces, or may have some other shape; and at least one internal surface adapted to be in contact with a medium undergoing a phase change at a temperature close to the temperature at which the surface is to be controlled. The phase change may either result in the generation of heat if the temperature of the surface is to be raised or the absorption of heat if the temperature of the surface is to be lowered. The device also includes a handle which, when connected to the roller, facilitates the rolling of the roller over the surface to be cooled. For preferred embodiments, the heat absorbing phase change is from solid to liquid, the medium for preferred embodiments being at least primarily water. The heat generating phase change may be from liquid to solid. For such embodiments, the roller may have a plurality of channels extending therethrough, the at least one internal surface being the walls of such channels. For preferred embodiments, there is a substantial number of such channels, each of which extend substantially parallel to the axis of the roller.

For alternative embodiments, the roller has a single channel formed therethrough, which channel is substantially parallel to the axis of the roller, and a mechanism is provided for chilling the walls of the channel. This mechanism may include a source of cryogen fluid and a mechanism for selectively applying the cryogen fluid to the walls of the channel, the fluid evaporating to chill such walls. The walls of the channel for this embodiment may be formed of a porous material and provide a greater surface area for chilling. Alternatively, the channel through the roller may contain at least two materials separated by a removable barrier, and materials undergoing an endoergic reaction when in contact with each other, which reaction results in the absorption of heat from the walls of the channel in contact therewith. Where the roller is being used to heat the surface, the two materials utilized might be ones which undergo an exothermic reaction when in contact with each other, which reaction results in the generation of heat to the internal surface(s). The barrier may for example be removable by being breakable and the materials utilized for this embodiment when used for cooling may be water and a suitable salt, the channel walls being of a corrosion resistant material where a salt is utilized. End caps may also be removably attachable to seal each end of the roller, with the handle being attachable to such end caps.

A temperature sensor may also be provided for the external surface, the temperature sensor for example being a temperature sensitive strip affixed to the external surface of the roller, a characteristic of the strip varying with temperature, or a thermocouple may be embedded in the external surface. A display may also be provided for the temperature sensor, the display for example being positioned in one of the end caps.

The invention also includes a method for manufacturing a cooling roller of a material having good heat transfer properties and a plurality of channels extending therethrough to cool a surface, the method including: filling the channels with a freezable liquid, freezing the liquid in the channels, the liquid expanding as it freezes, removing excess frozen liquid and sealing the roller at each of its ends. The roller is utilized by rolling the roller over the surface to be cooled, the liquid in the channels contracting as the liquid thaws to generate a partial vacuum which further facilitates the sealing of the roller. The rolling of the roller over the surface may be repeated as required to achieve a desired cooling, and/or the roller may after a period of use, be refrozen as required for subsequent use.

The invention also includes a method for controlling the temperature of a patient's skin which includes providing a roller having a material contained therein and in contact with at least one internal surface of the roller, which material is in a state which causes the roller to be at a temperature close to the temperature to which the patient's skin is to be controlled; and rolling the roller over a surface of the patient's skin at a rate so as to bring the skin surface to the controlled temperature, the material selectively undergoing a state change as the roller is being rolled over the skin surface. The material may initially be in a solid, frozen state and undergo a gradual change to a liquid state during the rolling step, the surface of the patient's skin being cooled during the rolling step to either precool the skin for a therapeutic treatment, to post-cool the skin after a therapeutic treatment or to perform a therapeutic treatment. Alternatively, the material may be initially in a heated liquid state and undergo a gradual change to a solid state during the rolling step to either preheat the surface of the patient's skin for a therapeutic treatment or to heat the surface of the patient's skin to perform a therapeutic treatment. Post-heating may also be performed. The rolling step may be performed under pressure resulting in at least some massaging of the patient's skin. For a particular embodiment, two rollers are provided, which rollers may be on the same handle, each having a material therein which is in a different state, the material in one roller heating the roller and the material in the other roller cooling the roller, the rollers being alternately rolled over an area of the patient's skin during the rolling step.

The foregoing and other objects, features and advantages of the invention will be apparent from the following more particular description of preferred embodiments of the invention as illustrated in the accompanying drawings, the same or similar reference numeral being used for like elements in the various figures.

DETAILED DESCRIPTION

FIGS. 1–5 show a first illustrative embodiment of the invention which is the currently preferred embodiment. The temperature control roller device 10 for this embodiment includes a roller 12 of a material with good heat transfer properties, or in other words of a material such as a metal, ceramic, certain plastics, sapphire or quartz having a high thermal conductivity. For a cooling embodiment of the invention currently being utilized, roller 12 is formed of copper or aluminum, copper having better heat transfer properties, but aluminum being less expensive. As may be best seen in FIGS. 4A and 4B, roller 12 has a center or axial channel 14 formed therethrough in which an axle 16 is mounted. A plurality of channels 18 are also formed through roller 12, thirty-eight such channels arranged in three concentric rings formed around axial channel 14 being shown for the illustrative embodiment. However, both the number of channels and their arrangement may vary with application. One factor in the arrangement of the channels is that each channel may more effectively conduct cold or heat to the roller surface if there is a solid path of thermally conductive material between the channel and the surface. For the embodiment shown, this is accomplished to some extent by having many of the channels in the various rings off-set from each other, a channel in one ring being between two channels in an adjacent ring. While for the illustrative embodiment, the channels decrease in size from the outer ring to the inner ring, this is also not a limitation on the invention, and the channels may all be of the same size or may vary in size in other ways. As may be best seen in FIG.

Figure 4A:
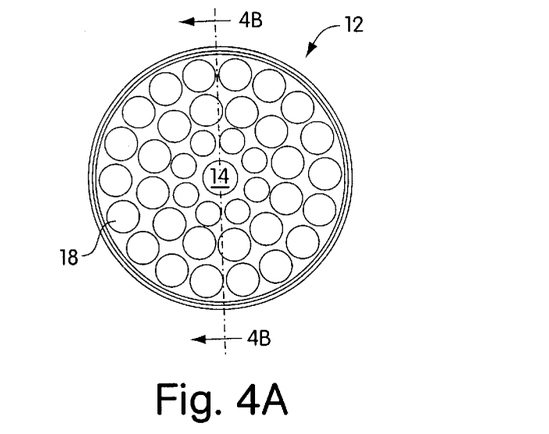
FIGS. 4A and 4B are side and front sectional views respectively of the roller for the embodiment shown in FIG. 1.
Figure 4B:
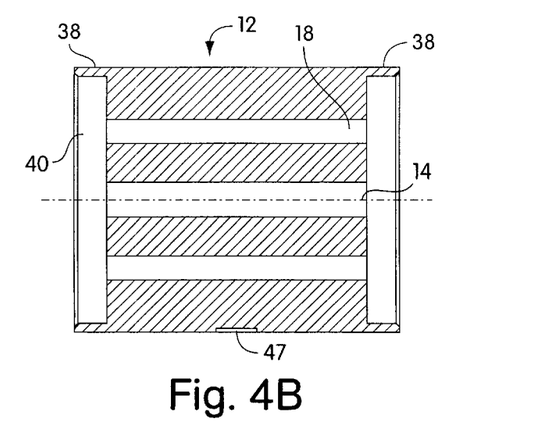
Figure 5:
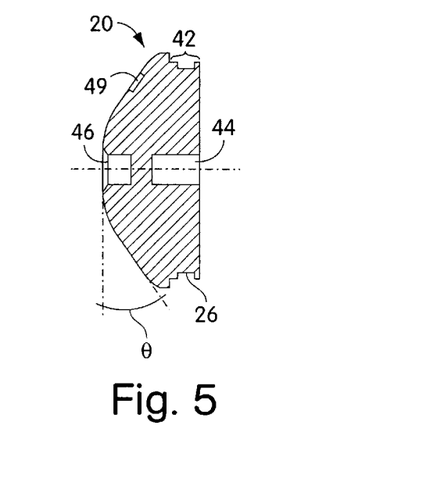
FIG. 5 is a side sectional view of an end cap for the embodiment of the invention shown in FIG. 1.

4A, the number of channels 18 and the size of each channel is such that the channels make up most of the interior of roller 12, forming 60% to 70% of the volume of the roller 12 for a current implementation, the walls of channel 18 thus providing roller 12 with a very large internal surface area. The interior walls of roller 12 between channels 18 may be relatively thin since structural integrity for the roller is provided primarily by the thicker outer wall of the roller. For the current implementation of the invention, roller 12 has a two inch diameter and the portion of the roller containing channels 18 is two inches long. A quarter inch flange 38 extends around each end of the roller to form a recess 40 at each roller end.

Figure 2:
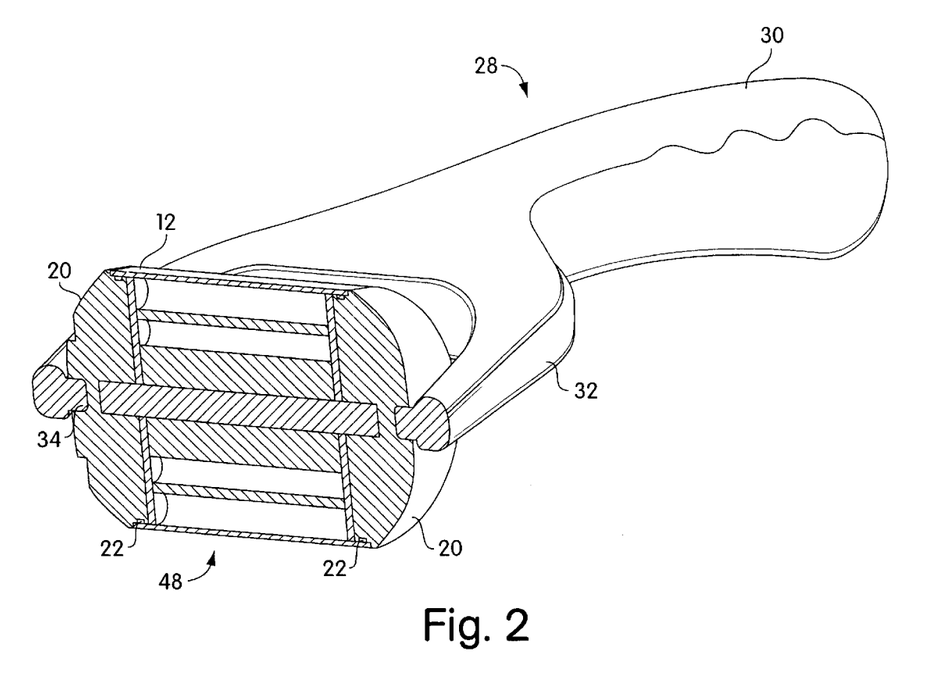
FIG. 2 is a partially cut-away top/front perspective view of the roller device of FIG. 1 when assembled.
Figure 3:
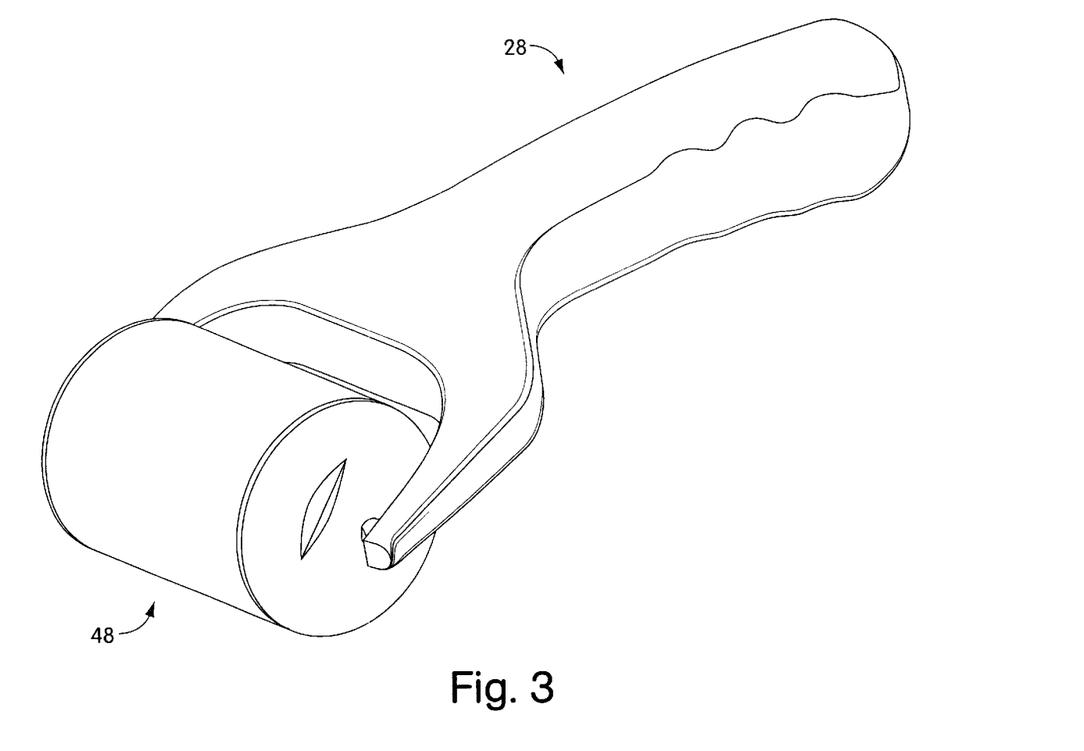
FIG. 3 is a top perspective view of the roller device of FIG. 1 when assembled.

Roller device 10 also has a pair of end caps 20, with a sealing ring 22 and a sealing washer 24 being provided for each end cap. As is best seen in FIG. 2, each sealing ring 22 fits in a sealing ring groove 26 (FIG. 5) formed in the corresponding end cap. For an alternative embodiment, axle 16 is replaced by a projection on each end cap, each of which fits into center channel 14 when the caps are mounted to the roller.

Figure 1:
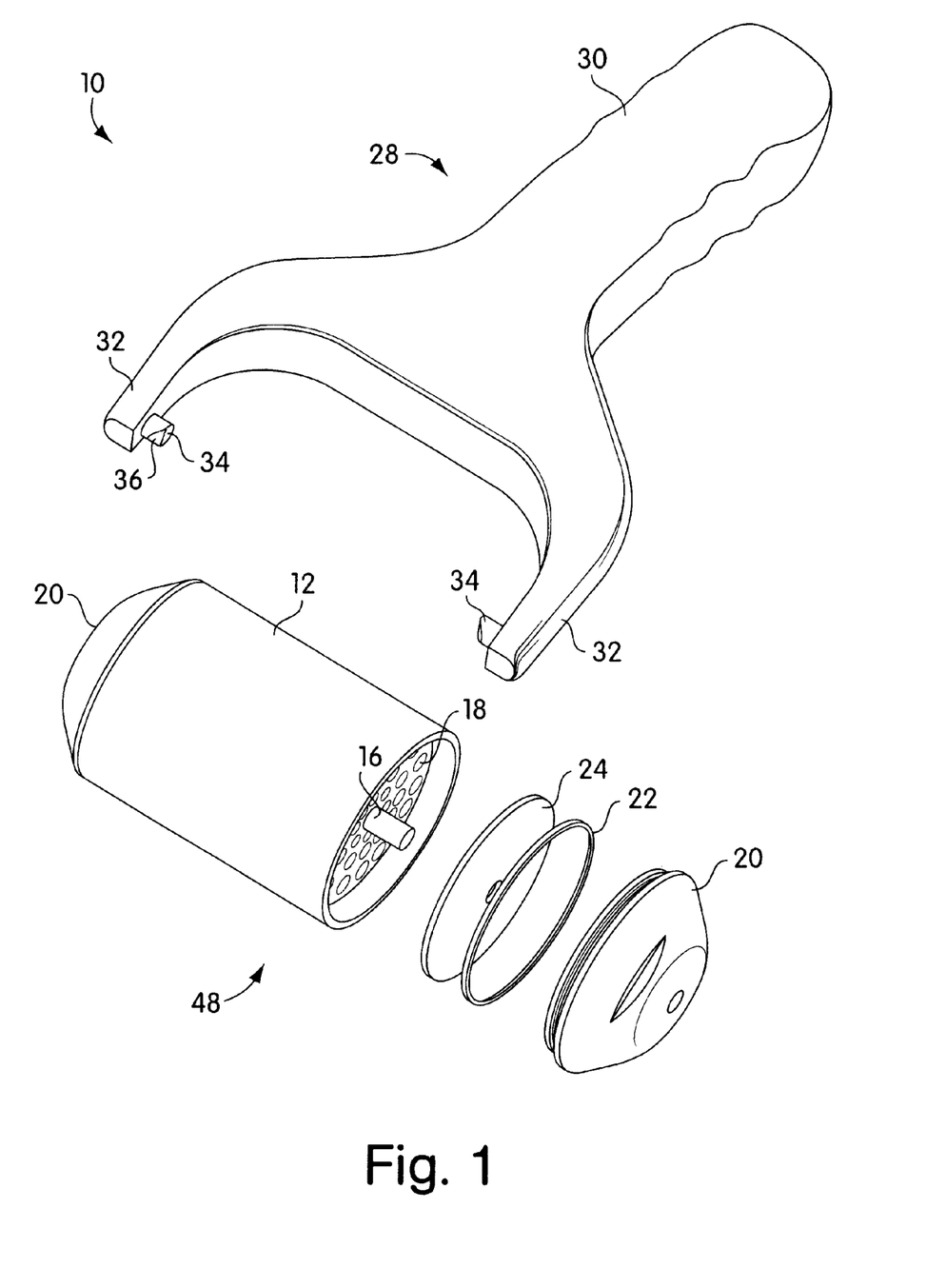
FIG. 1 is an exploded top perspective view of a temperature control roller device in accordance with a preferred embodiment of the invention.

Finally, roller device 10 has a handle 28 which includes a grip 30 at a proximal end thereof and splits into a pair of arms 32 at its distal end, each arm 32 having a projection 34 extending inward therefrom. The outer side of each projection 34 is an angled surface 36. Handle 28 is made of a plastic having sufficient resiliency so that arms 32 may be spread slightly, for reasons discussed later, and will then snap back to their original position.

As may be best seen in FIG. 2, when roller device 10 is assembled, each sealing washer 24 sits in recess 40 in the corresponding end of the roller and covers the ends of channels 18. Washer 24 has an axial hole through which axis 16 or the projection on the end cap passes. Each end cap 20 has a projecting portion 42 which fits in corresponding recess 40, the corresponding sealing ring 22 creating a pressure fit between projection 42 and the walls of recess 40. Each end cap also has an internal opening 44 sized and positioned to receive the end of axle 16 when cap 20 is assembled to roller 12 and an external opening 46 which flares slightly near the surface of the cap. The walls of cap 20 are also angled at an angle θ, for example 45°. The angled walls, in conjunction with angled surfaces 36 on projections 34 of handle 28, result in arms 32 of the handle being cammed apart as the handle is forced over roller assembly 48, the roller assembly including roller 12 and end caps 20. When projections 34 come adjacent openings 46, they drop into the opening as shown in FIG. 2, permitting arms 32 to return to their normal position. Projections 34 then serve as an axis about which the roller assembly may rotate, and the arms 32 also function to hold the roller assembly together, eliminating the need for the caps to be screwed, pinned, or otherwise secured to roller 12.

A temperature sensor 47 (FIG. 4B) may also be mounted to or embedded in the outer surface of roller 12 to assure that the roller device 10 is not used when its surface temperature is below a selected threshold or otherwise outside a selected range. Sensor 47 may be a thermocouple embedded in the outer surface of the roller which, for example, connects to an LCD or other suitable display 49 (FIG. 5) mounted for example on or in one of the end caps; or may be an adhesive strip the color of which changes with temperature in the relevant range, the color of the strip being indicative of roller surface temperature. Other suitable sensors could also be utilized, and the sensor could also be used to indicate when a roller assembly being chilled in a freezer is ready for use.

In operation, one of the end caps 20 is mounted to roller 12 in the manner described above and the roller is then filled with a suitable liquid. For a preferred embodiment, the liquid filling each channel 18 is either water or, for cooling applications, water with a suitable additive to slightly reduce its freezing temperature. For heating applications, a substance such as a paraffin could be used, which material solidifies from a liquid to a solid state at a temperature slightly above body temperature, for example a temperature of 37° C. to 45° C. Once all channels 14,18 of the roller are filled, it is, for cooling applications, placed in a freezer for a sufficient period of time for the fluid therein to freeze. For an illustrative embodiment, this period is less than two hours. Since the liquid in channels 18 will expand when frozen, it is preferable that the second end cap 20 not be mounted to roller 12 during this initial freezing operation and that the partial roller assembly instead be mounted in a rack or other suitable structure when being frozen so as to maintain the roller assembly in a position with the mounted end cap on the bottom.

Once the liquid in the roller has been frozen, the roller subassembly may be removed from the freezer. Excess frozen material resulting from the expansion of the material during freezing is then preferably removed before the second end cap and its associated washer are mounted to form the complete roller assembly 48. While this step may be performed when it is desired to use a roller, or could be performed for several rollers in for example a rack at one time, it is preferable that the sealed roller assemblies 48 be fabricated at the factory and shipped ready for use. Roller assemblies may be returned to the freezer at least several hours before use and retrieved as needed.

When there is a need to cool a surface, a roller is removed from the freezer and handle 28 is snapped in place on roller assembly 48 in the manner discussed above. The roller is then rolled over the surface to be cooled. The roller may for example be rolled over the surface to be treated at a rate of 0.5 to 1.5 inches per second for the illustrative embodiment and may for example precool an area of up to approximately 400 cm$^2$. While the temperature of the roller surface will typically be in the range of plus or minus 5° C. when removed from the freezer and will remain in this range for a period of about two hours when used at room temperature, the temperature to which the surface, for example the skin surface of a patient, is cooled depends on a number of factors, including the temperature of the roller surface, the rate at which the roller is being rolled over the surface and the number of times the roller passes over a particular spot on the surface, and the dwell time of the roller on the surface. The dwell time also controls the depth in the skin of cooling. For shallow depth of cooling, a minimum dwell time of roughly 10 seconds is generally required, with a dwell time of roughly one minute being preferred. For deep cooling in the skin, a dwell time which may be up to roughly thirty minutes may be required. Deep cooling may be useful for pain reduction in some procedures and possibly for treating fat. The skin or other surface, for the illustrative embodiment, remain at approximately 20° C. for roughly five minutes after treatment, and will then slowly return to normal body temperature.

While roller device 10 is being rolled over the surface to be treated, the roller may also be spreading a thin layer of a suitable liquid, gel or other material over the surface, which material fills in microroughness, cracks and other indentations in the surface, provides optical impedance matching and may perform other functions to enhance an optical dermatology treatment on a patient's skin or to enhance a procedure performed on some other type of surface. Alternatively, the roller may, for example, in addition to chilling the skin to reduce pain, also spread an antiseptic or other substance over the skin surface to further reduce pain, itching, or for some other therapeutic function.

As the frozen liquid in the roller assembly thaws, the sealing of the roller assembly to prevent leakage becomes more critical. However, since the excess material resulting from freezing of the liquid was removed prior to sealing of the roller assembly, and since the ends of the channels are sealed, as the material in the channels shrinks as a result of thawing, a partial vacuum is created in each channel which operates on washers 24 and on caps 20 to enhance the seal.

One problem with prior art cooling devices is that as the ice melts, a water barrier may form between the surface in contact with the skin and the remaining ice, thereby reducing the effectiveness of the remaining ice in chilling the contacting surface. However, the large number of channels for the illustrative embodiment, and the resulting large wall surface area, in conjunction with the rolling of the roller in general, and centrifugal force caused by such rolling, results in any remaining ice in the roller being moved into contact with a wall of the channel so that, so long as there is still some ice in the channels, the temperature of the roller, particularly when the roller is in use and being rolled, can be maintained close to the freezing temperature of the water or other substance with which the channels are filled. For an illustrative embodiment, a roller may be used for up to two hours without refreezing.

Once the ice within a roller has substantially thawed, arms 32 of handle 28 may be manually pulled apart sufficiently to permit the roller assembly to be removed from handle 28 and a new roller may be snapped into place. The roller which has been removed may be returned to the freezer for refreezing. Once a roller assembly has been sealed, the cycle of refreezing and using a roller may be repeated numerous times, theoretically a virtually unlimited number of times, before it is necessary to either refill or dispose of the roller.

Figure 6:
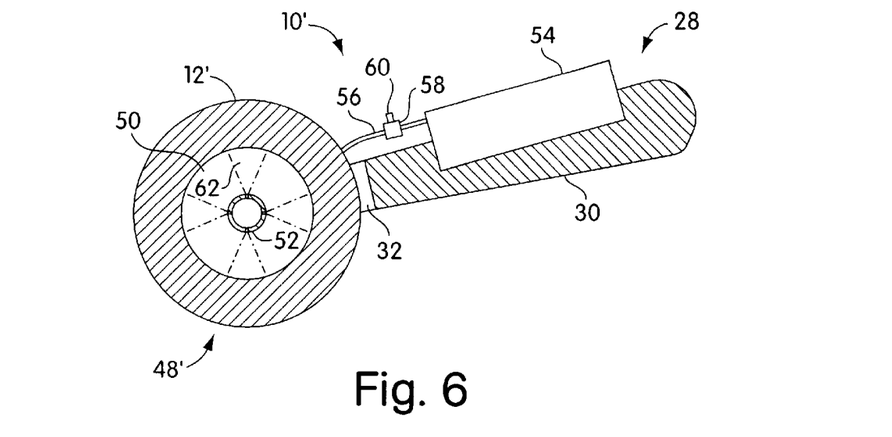
FIGS. 6 and 7 are side sectional views of two alternative embodiments of the invention.

FIG. 6 illustrates an alternative embodiment of the invention wherein the roller 12', instead of having a plurality of channels 18 which are filled with a freezable liquid, has a single internal channel 50 having a nozzle 52 extending therein from one of the end caps 20. Nozzle 52 is connected to a source of cryogen fluid 54, which source is mounted to handle portion 30 for the illustrative embodiment, through a tube 56 having a control valve 58 mounted therein. For the illustrative embodiment shown, valve 58 is manually operated by a button 60. Thus, when button 60 is operated, a spray 62 of cryogen fluid is applied to the walls of channel 50, the spray condensing on the walls of the channel and evaporating to cool the thermally conductive material of roller 12' and thus the outer surface of the roller. The walls of channel 50 may be formed of a porous material, may be ridged, or may otherwise have indentations or holes formed therein to increase the surface area on which condensation and evaporation occurs and to thus enhance the cooling effect. An operator may periodically operate button 60 as required to maintain roller 12' at a desired temperature, or the operator may hold down button 60 when the roller is in use, and valve 58 may be designed to periodically apply spray to nozzles 52 so long as button 60 is depressed to thus maintain the outer surface of roller 12' at a desired temperature. Alternatively, either once button 60 has been depressed, or while button 60 is depressed, a temperature sensor 47 either on or embedded in roller assembly 48', may be utilized to sense the surface temperature of the roller, the output from the temperature sensor being applied to a suitable control of valve mechanism 58 to open the valve to apply cryogen to the walls of channel 50 when the surface temperature of the roller drops below a selected threshold. Other control mechanisms are also possible. Cryogen source 54 is periodically replaced as required.

Figure 7:
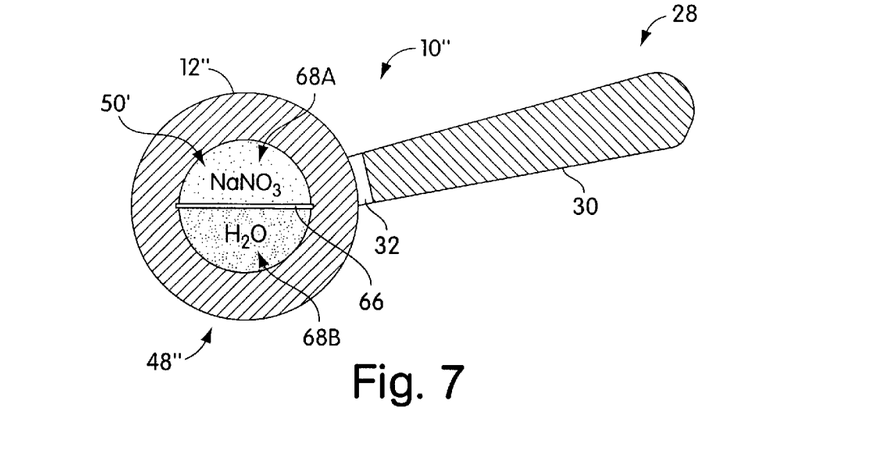

FIG. 7 shows another alternative embodiment of the invention, the roller device 10" of this embodiment having a center channel 50' which is divided into two subchannels by a removable barrier 66, channel portions 68A and 68B of channel 50' containing materials which react endoergically with each other so that, when the materials come together, they undergo a chemical reaction which absorbs heat. For an illustrative embodiment, channel section 68A is shown as containing $NaNO_3$ and channel section 68B is shown as containing water. Other materials undergoing endoergic reaction could also be utilized. While barrier 66 can be removable by being pulled out in some suitable manner, for an illustrative embodiment, the barrier is breakable by for example striking roller 12" or the corresponding roller assembly 48" on a hard surface, or, where the roller has slight flexibility, by slightly flexing the roller to break the barrier. Other techniques for selectively removing barrier 66 are also within the contemplation of the invention. A roller 12", or roller assembly 48", would typically be a single use item and would be disposable after use.

Where roller device is being used for heating, the roller assembly would be filled and sealed as for the cooling embodiment, except without the freezing and trimming steps. The fill for the channels could be a liquid as previously discussed or could be a suitable gel or other semi-solid. For a preferred implementation, the fill is a material such as a paraffin which is a solid at room or normal body temperature, but is a liquid at slightly higher temperatures. This material would be heated to its liquid state and give off substantial heat as it returns or "freezes" to its solid state. Alternatively, where the fill is a liquid such as water, the liquid could be heated above its evaporation temperature so that all or a substantial portion of the liquid passes into its gaseous state, and then condense to its liquid state in use. For this embodiment, a vent, preferably a one-way vent, would need to be provided for example on the end caps to permit sufficient gas to escape, so that the pressure in the chambers is lowered sufficiently both to prevent the end caps from being blown off or rupturing of the roller and to permit evaporation. In lieu of vents, the seal could be such that at some pressure, gas can escape through the seal. However, once the gas escapes, particularly as the liquid condenses, vacuum pressure would be applied to the seal and end cap to hold the assembly together preventing leakage of liquid or gas.

When it was desired to use the roller device, the roller assembly would be heated to a desired temperature in an oven, boiling water, a microwave oven, or other suitable heating device. If the roller assembly is to be microwave heatable, the roller 12 would either need to be formed of a microwave compatible material, for example a ceramic, or modified to be microwave compatible. The large surface area of the roller in contact with the heated material would also be advantageous for heating, and the mixing action of the fluid sloshing in the channels would maintain the walls of the channels at a substantially uniform temperature. Where a roller 12" of FIG. 7 is used for a heating application, the materials in the subchannels 68A and 68B would be materials undergoing an exothermic or heat generating reaction when brought into contact with each other. As for cooling, the skin surface temperature and depth of heating would depend on many factors including temperature of the roller surface, and dwell time on a surface area, dwell time for example depending on the rate the roller is rolled over the surface and on the number of passes. Dwell time for heating would generally be comparable to those for cooling.

Figure 8A:
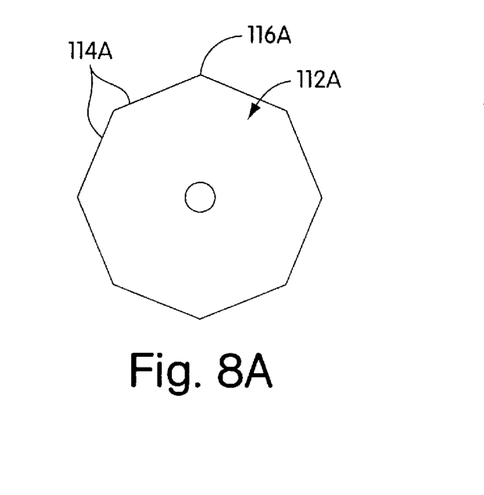
FIGS. 8A and 8B are sectional views for two alternative roller shapes.
Figure 8B:
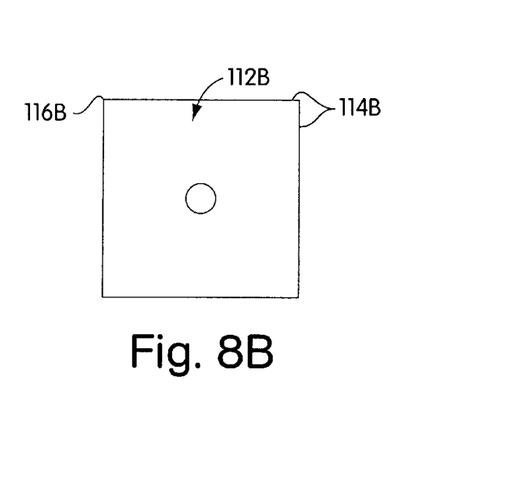

One advantage of the various embodiments of the invention, whether used for heating or cooling, is that the roller device also applies pressure to the surface which, where the surface is a patient's skin, can result is deeper heating/cooling and, by eliminating blood under the roller, can extend the period the skin maintains the desired lower/higher temperature by reducing profusion induced temperature moderation. The pressure may also have a therapeutic massaging effect on the skin and on muscles or other body components underlying the skin. The therapeutic massage effect either with heat or with cold may be enhanced by having a roller such as roller 112A of FIG. 8A which has for example an octagonal cross-section rather than a circular cross-section with corners 116A between each pair of adjacent faces 114A. FIG. 8B illustrates another alternative roller shape wherein the roller 112B has a square cross-section with four faces 114B and corners 116B therebetween. While two alternative roller shapes 112A and 112B have been shown in the figures, it is apparent that other alternative roller shapes may be utilized having either a greater or lesser number of faces 114 and that, while in the figures the faces 114 have been shown as being flat, this is also not a limitation on the invention, and that each of the faces 114 may have either a convex or concave curve which may, for example, be a circular arc having a smaller diameter than that of the roller 112 or may be in the form of a parabolic, elliptical or other suitable curve. Particularly with the embodiment of FIG. 8B, rather then continually rolling the roller over the treatment surface, each face 114 may be brought into contact with the surface and left in contact until its temperature starts to equalize with that of the surface, and then the next surface brought into contact. Between periods of contact, the medium returns a surface 114 to the desired temperature.

While in the discussion above, the various roller devices 10 have been indicated as usable for pretreatment of the surface or to effect a desired therapeutic treatment, it is also possible for the roller devices to be used for post-treatment, for example to cool a skin surface after treatment to reduce pain, cool the skin to minimize thermal damage and/or to reduce swelling. It is also possible, for massage or other treatments, to provide two rollers 12, one to heat the skin and one to cool the skin, which rollers may be mounted to the same handle 28 or to different handles, and which rollers are applied alternatively to the skin to alternately heat and cool the skin to effect the desired therapeutic treatment.

While the invention has been particularly shown and described above with reference to several embodiments, and variations on these embodiments have been discussed, it is to be understood that these embodiments have been shown for purposes of illustration only and that other variations are within the contemplation of the invention. For example, the handle 28 shown may be replaced with a handle extending from the roller axis or with other shapes or forms of handles, and it is possible that in some applications, a handle may not be required. For example, for treatment by the patient on the patient's back or other areas, one or more rollers may be mounted in an elongated support with hand holds at the ends, permitting the rollers to be rolled over the surface as the support is pulled back and forth over the surface. Therefore, the foregoing and other changes in form and detail may be made in the invention by one skilled in the art while still remaining within the spirit and scope of the invention which is to be defined only by the appended claims.

What is claimed is:

1. A device for cooling a surface including:
    a roller formed of a material having good heat transfer properties, said roller having an external surface and a plurality of internal channels formed therethrough, each of said channels having internal walls adapted to be in contact with a medium undergoing a heat absorbing phase change; and
    a handle which, when connected to the roller, facilitates the rolling of the roller over the surface to be cooled.
2. A device as claimed in claim 1 wherein the roller is formed of a metal.
3. A device as claimed in claim 1 wherein said external surface is cylindrical.
4. A device as claimed in claim 1 wherein said external surface has a plurality of faces.
5. A device as claimed in claim 4 wherein said faces are substantially flat.
6. A device as claimed in claim 1 wherein said medium is in each of said channels, and wherein said heat absorbing phase change of the medium is from solid to liquid.
7. A device as claimed in claim 6 wherein said medium is at least primarily water.
8. A device as claimed in claim 1 wherein said roller has an axis and each of said channels extends substantially parallel to said axis.
9. A device as claimed in claim 1 wherein said roller has opposed ends, and including an end cap attachable to seal each end.
10. A device as claimed in claim 9 wherein said handle attaches to said end caps.
11. A device as claimed in claim 9 wherein said medium is sealed in said roller.
12. A device as claimed in claim 1 including a temperature sensor for said external surface.
13. A device as claimed in claim 12 wherein said temperature sensor is selected from the group consisting of a temperature sensitive strip affixed to said external surface, a characteristic of which varies with temperature, and a thermocouple embedded in said external surface.
14. A device as claimed in claim 12 including a display for said temperature sensor.
15. A device for controlling the temperature of a surface including:
    a roller formed of a material having good heat transfer properties, said roller having an external surface and a plurality of channels extending therethrough, each of said channels having internal walls adapted to be in contact with a heat transfer medium which undergoes a phase change at a temperature close to the temperature at which the surface is to be controlled, which phase change results in one of the generation of heat if the temperature of the surface is to be raised and the absorption of heat if the temperature of the surface is to be lowered; and
    a handle which, when connected to the roller, facilitates the rolling of the roller over the surface the temperature of which is to be controlled.
16. A device as claimed in claim 15 wherein the roller is formed of a metal.
17. A device as claimed in claim 15 wherein said external surface is cylindrical.
18. A device as claimed in claim 15 wherein said external surface has a plurality of faces.
19. A device as claimed in claim 18 wherein said faces are substantially flat.
20. A device as claimed in claim 15 wherein said heat transfer medium is in each of said channels, and wherein said heat absorbing phase change of the medium is from solid to liquid.

21. A device as claimed in claim 15 wherein the heat generating phase change is from liquid to solid.

22. A device as claimed in claim 15 wherein said roller has opposed ends, and including an end cap attachable to seal each end.

23. A device as claimed in claim 15 wherein said medium is sealed in said roller.

24. A device as claimed in claim 15 including a temperature sensor for said external surface.

25. A device as claimed in claim 24 wherein said temperature sensor is selected from the group consisting of a temperature sensitive strip affixed to said external surface, a characteristic of which varies with temperature, and a thermocouple embedded in said external surface.

26. A device as claimed in claim 24 including a display for said temperature sensor.

27. A method for controlling the temperature of a patient's skin including:
providing a roller having a material contained therein and in contact with internal walls of a plurality of channels formed in the roller, which material is in a state which causes the roller to be at a temperature close to the temperature to which the patient's skin is to be controlled; and
rolling the roller over a surface of the patient's skin at a rate so as to bring the skin surface to the controlled temperature, the material selectively undergoing a state change as the roller is being rolled over the skin surface.

28. A method as claimed in claim 27 wherein the material is initially in a solid frozen state and undergoes a gradual change to a liquid state during said rolling step, the surface of the patient's skin being cooled during said rolling step.

29. A method as claimed in claim 27 wherein the material is initially in a heated liquid state and undergoes a gradual change to a solid state during said rolling step to heat the surface of the patient's skin.

30. A method as claimed in claim 27 wherein said rolling step is performed under pressure resulting in at least some massaging of the patient's skin.

31. A method as claimed in claim 27 wherein, during said providing step, first and second rollers are provided, each having a material therein which is in a different state, the material in the first roller heating the first roller and the material in the second roller cooling the second roller; and wherein, during said rolling step, said first and second rollers are alternately rolled over an area of the patient's skin.

32. A roller adapted for use in a device for controlling a surface's temperature, the roller having an external surface and a plurality of internal channels, each said channel being sealed to seal therein a heat transfer medium which undergoes a phase change at a temperature close to the temperature at which the surface is to be controlled and having walls adapted to be in contact with said heat transfer medium.

* * * * *